(12) United States Patent
Cappello et al.

(10) Patent No.: US 9,932,389 B2
(45) Date of Patent: Apr. 3, 2018

(54) SILK-ELASTIN LIKE PROTEIN POLYMERS FOR EMBOLIZATION AND CHEMOEMBOLIZATION TO TREAT CANCER

(71) Applicant: THE UNIVERSITY OF UTAH RESEARCH FOUNDATION, Salt Lake City, UT (US)

(72) Inventors: Joseph Cappello, San Diego, CA (US); Hamidreza Ghandehari, Salt Lake City, UT (US); Azadeh Poursaid, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/064,142

(22) Filed: Mar. 8, 2016

(65) Prior Publication Data
US 2016/0176949 A1 Jun. 23, 2016

Related U.S. Application Data

(62) Division of application No. 14/150,652, filed on Jan. 8, 2014, now abandoned.

(60) Provisional application No. 61/848,673, filed on Jan. 8, 2013.

(51) Int. Cl.
| | |
|---|---|
| *C07K 14/78* | (2006.01) |
| *A61K 38/39* | (2006.01) |
| *A61K 47/42* | (2017.01) |
| *A61K 45/06* | (2006.01) |
| *A61K 9/00* | (2006.01) |
| *C07K 14/435* | (2006.01) |
| *A61K 38/17* | (2006.01) |

(52) U.S. Cl.
CPC ............ *C07K 14/78* (2013.01); *A61K 9/0019* (2013.01); *A61K 9/0024* (2013.01); *A61K 38/1767* (2013.01); *A61K 38/39* (2013.01); *A61K 45/06* (2013.01); *A61K 47/42* (2013.01); *C07K 14/43586* (2013.01)

(58) Field of Classification Search
CPC ......... C07K 14/78; A61K 38/39; A61K 47/42
See application file for complete search history.

(56) References Cited

U.S. PATENT DOCUMENTS

| | | |
|---|---|---|
| 2001/0018445 A1 | 8/2001 | Huang et al. |
| 2003/0176355 A1 | 9/2003 | Cappello et al. |
| 2005/0227910 A1 | 10/2005 | Yang et al. |
| 2009/0246283 A1 | 10/2009 | Kumar |
| 2011/0129531 A1 | 6/2011 | Collette et al. |
| 2012/0282300 A1 | 11/2012 | Masters et al. |
| 2013/0011467 A1 | 1/2013 | Zhang et al. |
| 2013/0022545 A1 | 1/2013 | Lee et al. |
| 2013/0059772 A1 | 3/2013 | Kumar |
| 2013/0195988 A1 | 8/2013 | Duan et al. |
| 2014/0086976 A1 | 3/2014 | Szalay et al. |

FOREIGN PATENT DOCUMENTS

| | | |
|---|---|---|
| WO | 2013181471 | 12/2013 |
| WO | 2014031693 | 2/2014 |

OTHER PUBLICATIONS

U.S. Appl. No. 14/150,652, Response to Non-Final Office Action, dated Aug. 25, 2015, 25 pages.
U.S. Appl. No. 14/150,652, Non-Final Office Action, dated Mar. 25, 2015, 13 pages.
U.S. Appl. No. 14/150,652, Final Office Action, dated Sep. 8, 2015, 10 pages.
Anumolu, et al., "Fabrication of highly uniform nanoparticles from recombinant Silk-elastin-like protein polymers for therapeutic agent delivery", ACS Nano, 5(7) Jul. 26, 2011, pp. 5374-5382.
Cappello, et al., "In-situ self-assembling protein polymer gel systems for administration, delivery, and release of drugs", Journal of Control Release, vol. 53, Apr. 30, 1998, pp. 105-117.
Gustafson, et al., "Silk-Elastinlike recombinant polymers for gene therapy of head and neck cancer; from molecular definition to controlled gene expression", Journal of Control Release, vol. 140, Dec. 16, 2009, pp. 265-261.
Gustafson, "Silk-Elastinlike Protein Polymers for Adenoviral Cancer Gene Therapy", Ph.D. Dissertation, The University of Utah, Doc. No. 3547213, Dec. 2012, 266 pages.
Gustafson, et al., "Silk-Elastinlike Protein Polymers for Matrix-Mediated Cancer Gene Therapy", Advanced Drug Delivery Reviews, vol. 62, Dec. 30, 2010, pp. 1509-1523.
Gustafson, et al., "Synthesis and characterization of a matrix-metalloproteinase responsive silk-esatinlike protein polymer", Biomacromolecules, vol. 14, Mar. 11, 2013, pp. 618-625.
Hu, et al., "Biomaterials derived from silk-tropoelastin protein systems", Biomaterials, vol. 31, Nov. 31, 2010, pp. 8121-8131.
Llovet, et al., "Systematic review of randomized trials for unresectable hepatocellular carcinoma: chemoembolization improves survival", Hepatology, vol. 37, No. 2, Feb. 2003, pp. 429-442.
Megeed, et al., "Genetically engineered silk-elastinlike protein polymers for controlled drug delivery", Advanced Drug Delivery Reviews, vol. 54, 2002, pp. 1075-1091.
Megeed, et al., "In vitro and in vivo evaluation of recombinant silk-elastinlike hydrogels for cancer gene therapy", Journal of Controlled Release, vol. 94, 2004, pp. 433-445.

(Continued)

*Primary Examiner* — Karen Cochrane Carlson
(74) *Attorney, Agent, or Firm* — Gardner Groff Greenwald & Villanueva, PC

(57) ABSTRACT

A chemoembolic agent is disclosed that includes an injectable, recombinantly synthesized silk-elastin like protein copolymer and one or more chemotherapeutic agents. Upon injection, the chemoembolic agent blocks the tumor vasculature, including the capillary bed, and may optionally release chemotherapeutic agents. The chemoembolic agent may be used to treat cancer, including hepatocellular carcinoma.

8 Claims, 12 Drawing Sheets

(56) References Cited

OTHER PUBLICATIONS

Numata, et al., "Silk-based delivery systems of bioactive molecules", Advanced Drug Delivery Reviews, vol. 62, 2010, pp. 1497-1508.
Poursaid, et al., "In situ gelling silk-elastinlike protein polymer for transarterial chemoembolization", Biomaterials, vol. 57, 2015, pp. 142-152.
Price, "Effect of shear on physicochemical properties of matrix metalloproteinase responsive silk-elastinlike hydrogels", Journal of Controlled Release, vol. 195, 2014, pp. 92-98.
Skjot-Arkil, et al., "Measurement of MMP-9 and -12 degraded elastin (ELM) provides unique information on lung tissue degradation", BMC Pulmonary Medicine, vol. 12, 2012, pp. 1-12.
Varela, et al., "Chemoembolization of hepatocellular carcinoma with drug eluting beads: Efficacy adn doxorubicin pharmacokinetics", Journal of Hepatology, vol. 46, 2007, pp. 474-481.

SELP-47K (SEQ ID NO: 3)

MDPVVLQRRDWENPGVTQLVRLAAHPPFASDPMGAGSGAGAGS[(GVGVP)₄GKGVP(GVGVP)₃(GAGAGS)₄]₁₂(GVGVP)₄GKGVP(GVGVP)₂(GAGAGS)₂GAMDPGRYQDLRSHHHHHH

SELP-815K (SEQ ID NO: 4)

MDPVVLQRRDWENPGVTQLNRLAAHPPFASDPM[GAGS(GAGAGS)₂GA]₆GAMDPGRYQDLRSHHHHHH(GVGVP)₄GKGVP(GVGVP)₁(GAGAGS)₅GA]₆GAMDPGRYQDLRSHHHHHH

FIG. 1A

SEQUENCE LISTING

<160> NUMBER OF SEQ ID NOS: 5

<210> SEQ ID NO 1
<211> LENGTH: 6

<212> TYPE: PRT
<213> ORGANISM: Bombyx mori

<400> SEQUENCE: 1

Gly Ala Gly Ala Gly Ser
1               5

<210> SEQ ID NO 2
<211> LENGTH: 5
<212> TYPE: PRT
<213> ORGANISM: Homo sapiens

<400> SEQUENCE: 2

Gly Val Gly Val Pro
1               5

<210> SEQ ID NO 3
<211> LENGTH: 877
<212> TYPE: PRT
<213> ORGANISM: Artificial Sequence
<220> FEATURE:
<223> OTHER INFORMATION: Combined copolymers of b. mori silk blocks and
      h. sapien elastin blocks

<400> SEQUENCE: 3

Met Asp Pro Val Val Leu Gln Arg Arg Asp Trp Glu Asn Pro Gly Val
1               5                   10                  15

Thr Gln Leu Val Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Lys Gly Val Pro Gly Lys Gly Val Pro Gly Val
65                  70                  75                  80

Gly Val Pro Gly Ala Gly Ala Gly Ser Gly Ala Gly Ala Gly Ser Gly
                85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

Lys Gly Val Pro Gly Lys Gly Val Pro Gly Lys Gly Val Pro Gly Val
    130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
                165                 170                 175

Gly Val Gly Val Pro Gly Val Gly Val Pro Gly Val Gly Val Pro Gly
            180                 185                 190

Lys Gly Val Pro Gly Lys Gly Val Pro Gly Lys Gly Val Pro Gly Val
        195                 200                 205

Gly Val Pro Gly Ala Gly Ala Gly Ser Gly Ala Gly Ala Gly Ser Gly
    210                 215                 220

Ala Gly Ala Gly Ser Gly Ala Gly Ala Gly Ser Gly Val Gly Val Pro
225                 230                 235                 240

Gly Val Gly Val Pro Gly Val Gly Val Pro Gly Val Gly Val Pro Gly
                245                 250                 255

Lys Gly Val Pro Gly Lys Gly Val Pro Gly Lys Gly Val Pro Gly Val

-continued

```
            260                 265                 270
Gly Val Pro Gly Ala Gly Ala Gly Ser Gly Ala Gly Ala Gly Ser Gly
            275                 280                 285

Ala Gly Ala Gly Ser Gly Ala Gly Ala Gly Ser Gly Val Gly Val Pro
            290                 295                 300

Gly Val Gly Val Pro Gly Val Gly Val Pro Gly Val Gly Val Pro Gly
305                 310                 315                 320

Lys Gly Val Pro Gly Lys Gly Val Pro Gly Lys Gly Val Pro Gly Val
            325                 330                 335

Gly Val Pro Gly Ala Gly Ala Gly Ser Gly Ala Gly Ala Gly Ser Gly
            340                 345                 350

Ala Gly Ala Gly Ser Gly Ala Gly Ala Gly Ser Gly Val Gly Val Pro
            355                 360                 365

Gly Val Gly Val Pro Gly Val Gly Val Pro Gly Val Gly Val Pro Gly
            370                 375                 380

Lys Gly Val Pro Gly Lys Gly Val Pro Gly Lys Gly Val Pro Gly Val
385                 390                 395                 400

Gly Val Pro Gly Ala Gly Ala Gly Ser Gly Ala Gly Ala Gly Ser Gly
            405                 410                 415

Ala Gly Ala Gly Ser Gly Ala Gly Ala Gly Ser Gly Val Gly Val Pro
            420                 425                 430

Gly Val Gly Val Pro Gly Val Gly Val Pro Gly Val Gly Val Pro Gly
            435                 440                 445

Lys Gly Val Pro Gly Lys Gly Val Pro Gly Lys Gly Val Pro Gly Val
            450                 455                 460

Gly Val Pro Gly Ala Gly Ala Gly Ser Gly Ala Gly Ala Gly Ser Gly
465                 470                 475                 480

Ala Gly Ala Gly Ser Gly Ala Gly Ala Gly Ser Gly Val Gly Val Pro
            485                 490                 495

Gly Val Gly Val Pro Gly Val Gly Val Pro Gly Val Gly Val Pro Gly
            500                 505                 510

Lys Gly Val Pro Gly Lys Gly Val Pro Gly Lys Gly Val Pro Gly Val
            515                 520                 525

Gly Val Pro Gly Ala Gly Ala Gly Ser Gly Ala Gly Ala Gly Ser Gly
            530                 535                 540

Ala Gly Ala Gly Ser Gly Ala Gly Ala Gly Ser Gly Val Gly Val Pro
545                 550                 555                 560

Gly Val Gly Val Pro Gly Val Gly Val Pro Gly Val Gly Val Pro Gly
            565                 570                 575

Lys Gly Val Pro Gly Lys Gly Val Pro Gly Lys Gly Val Pro Gly Val
            580                 585                 590

Gly Val Pro Gly Ala Gly Ala Gly Ser Gly Ala Gly Ala Gly Ser Gly
            595                 600                 605

Ala Gly Ala Gly Ser Gly Ala Gly Ala Gly Ser Gly Val Gly Val Pro
            610                 615                 620

Gly Val Gly Val Pro Gly Val Gly Val Pro Gly Val Gly Val Pro Gly
625                 630                 635                 640

Lys Gly Val Pro Gly Lys Gly Val Pro Gly Lys Gly Val Pro Gly Val
            645                 650                 655

Gly Val Pro Gly Ala Gly Ala Gly Ser Gly Ala Gly Ala Gly Ser Gly
            660                 665                 670

Ala Gly Ala Gly Ser Gly Ala Gly Ala Gly Ser Gly Val Gly Val Pro
            675                 680                 685
```

```
Gly Val Gly Val Pro Gly Val Gly Val Pro Gly Val Gly Val Pro Gly
        690                 695                 700
Lys Gly Val Pro Gly Lys Gly Val Pro Gly Lys Gly Val Pro Gly Val
705                 710                 715                 720
Gly Val Pro Gly Ala Gly Ala Gly Ser Gly Ala Gly Ala Gly Ser Gly
            725                 730                 735
Ala Gly Ala Gly Ser Gly Ala Gly Ala Gly Ser Gly Val Gly Val Pro
        740                 745                 750
Gly Val Gly Val Pro Gly Val Gly Val Pro Gly Val Gly Val Pro Gly
            755                 760                 765
Lys Gly Val Pro Gly Lys Gly Val Pro Gly Lys Gly Val Pro Gly Val
        770                 775                 780
Gly Val Pro Gly Ala Gly Ala Gly Ser Gly Ala Gly Ala Gly Ser Gly
785                 790                 795                 800
Ala Gly Ala Gly Ser Gly Ala Gly Ala Gly Ser Gly Val Gly Val Pro
            805                 810                 815
Gly Val Gly Val Pro Gly Val Gly Val Pro Gly Val Gly Val Pro Gly
        820                 825                 830
Lys Gly Val Pro Gly Val Gly Val Pro Gly Val Gly Val Pro Gly Ala
            835                 840                 845
Gly Ala Gly Ser Gly Ala Gly Ala Gly Ser Gly Ala Met Asp Pro Gly
        850                 855                 860
Arg Tyr Gln Asp Leu Arg Ser His His His His His His
865                 870                 875

<210> SEQ ID NO 4
<211> LENGTH: 820
<212> TYPE: PRT
<213> ORGANISM: Artificial Sequence
<220> FEATURE:
<223> OTHER INFORMATION: Combined copolymers of b. mori silk blocks and
      h. sapien elastin blocks

<400> SEQUENCE: 4

Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
            20                  25                  30
Met Gly Ala Gly Ser Gly Ala Gly Ala Gly Ser Gly Ala Gly Ala Gly
        35                  40                  45
Ser Gly Val Gly Val Pro Gly Val Gly Val Pro Gly Val Gly Val Pro
50                  55                  60
Gly Val Gly Val Pro Gly Lys Gly Val Pro Gly Val Gly Val Pro Gly
65                  70                  75                  80
Val Gly Val Pro Gly Val Gly Val Pro Gly Val Gly Val Pro Gly Val
            85                  90                  95
Gly Val Pro Gly Val Gly Val Pro Gly Val Gly Val Pro Gly Val Gly
            100                 105                 110
Val Pro Gly Val Gly Val Pro Gly Val Gly Val Pro Gly Val Gly Val
        115                 120                 125
Pro Gly Ala Gly Ala Gly Ser Gly Ala Gly Ala Gly Ser Gly Ala Gly
        130                 135                 140
Ala Gly Ser Gly Ala Gly Ala Gly Ser Gly Ala Gly Ala Gly Ser Gly
145                 150                 155                 160
Ala Gly Ala Gly Ser Gly Ala Gly Ala Gly Ser Gly Ala Gly Ala Gly
```

```
                     165                 170                 175
Ser Gly Val Gly Val Pro Gly Val Gly Val Pro Gly Val Gly Val Pro
                180                 185                 190
Gly Val Gly Val Pro Gly Lys Gly Val Pro Gly Val Gly Val Pro Gly
                195                 200                 205
Val Gly Val Pro Gly Val Gly Val Pro Gly Val Gly Val Pro Gly Val
                210                 215                 220
Gly Val Pro Gly Val Gly Val Pro Gly Val Gly Val Pro Gly Val Gly
225                 230                 235                 240
Val Pro Gly Val Gly Val Pro Gly Val Gly Val Pro Gly Val Gly Val
                245                 250                 255
Pro Gly Ala Gly Ala Gly Ser Gly Ala Gly Ala Gly Ser Gly Ala Gly
                260                 265                 270
Ala Gly Ser Gly Ala Gly Ala Gly Ser Gly Ala Gly Ala Gly Ser Gly
                275                 280                 285
Ala Gly Ala Gly Ser Gly Ala Gly Ala Gly Ser Gly Ala Gly Ala Gly
                290                 295                 300
Ser Gly Val Gly Val Pro Gly Val Gly Val Pro Gly Val Gly Val Pro
305                 310                 315                 320
Gly Val Gly Val Pro Gly Lys Gly Val Pro Gly Val Gly Val Pro Gly
                325                 330                 335
Val Gly Val Pro Gly Val Gly Val Pro Gly Val Gly Val Pro Gly Val
                340                 345                 350
Gly Val Pro Gly Val Gly Val Pro Gly Val Gly Val Pro Gly Val Gly
                355                 360                 365
Val Pro Gly Val Gly Val Pro Gly Val Gly Val Pro Gly Val Gly Val
                370                 375                 380
Pro Gly Ala Gly Ala Gly Ser Gly Ala Gly Ala Gly Ser Gly Ala Gly
385                 390                 395                 400
Ala Gly Ser Gly Ala Gly Ala Gly Ser Gly Ala Gly Ala Gly Ser Gly
                405                 410                 415
Ala Gly Ala Gly Ser Gly Ala Gly Ala Gly Ser Gly Ala Gly Ala Gly
                420                 425                 430
Ser Gly Val Gly Val Pro Gly Val Gly Val Pro Gly Val Gly Val Pro
                435                 440                 445
Gly Val Gly Val Pro Gly Lys Gly Val Pro Gly Val Gly Val Pro Gly
                450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Val Gly
                485                 490                 495
Val Pro Gly Val Gly Val Pro Gly Val Gly Val Pro Gly Val Gly Val
                500                 505                 510
Pro Gly Ala Gly Ala Gly Ser Gly Ala Gly Ala Gly Ser Gly Ala Gly
                515                 520                 525
Ala Gly Ser Gly Ala Gly Ala Gly Ser Gly Ala Gly Ala Gly Ser Gly
                530                 535                 540
Ala Gly Ala Gly Ser Gly Ala Gly Ala Gly Ser Gly Ala Gly Ala Gly
545                 550                 555                 560
Ser Gly Val Gly Val Pro Gly Val Gly Val Pro Gly Val Gly Val Pro
                565                 570                 575
Gly Val Gly Val Pro Gly Lys Gly Val Pro Gly Val Gly Val Pro Gly
                580                 585                 590
```

-continued

```
Val Gly Val Pro Gly Val Gly Val Pro Gly Val Gly Val
        595                 600                 605

Gly Val Pro Gly Val Gly Val Pro Gly Val Gly Val Pro Gly Val Gly
610                 615                 620

Val Pro Gly Val Gly Val Pro Gly Val Gly Val Pro Gly Val Gly Val
625                 630                 635                 640

Pro Gly Ala Gly Ala Gly Ser Gly Ala Gly Ala Gly Ser Gly Ala Gly
            645                 650                 655

Ala Gly Ser Gly Ala Gly Ala Gly Ser Gly Ala Gly Ala Gly Ser Gly
            660                 665                 670

Ala Gly Ala Gly Ser Gly Ala Gly Ala Gly Ser Gly Ala Gly Ala Gly
            675                 680                 685

Ser Gly Val Gly Val Pro Gly Val Gly Val Pro Gly Val Gly Val Pro
    690                 695                 700

Gly Val Gly Val Pro Gly Lys Gly Val Pro Gly Val Gly Val Pro Gly
705                 710                 715                 720

Val Gly Val Pro Gly Val Gly Val Pro Gly Val Gly Val Pro Gly Val
            725                 730                 735

Gly Val Pro Gly Val Gly Val Pro Gly Val Gly Val Pro Gly Val Gly
            740                 745                 750

Val Pro Gly Val Gly Val Pro Gly Val Gly Val Pro Gly Val Gly Val
            755                 760                 765

Pro Gly Ala Gly Ala Gly Ser Gly Ala Gly Ala Gly Ser Gly Ala Gly
            770                 775                 780

Ala Gly Ser Gly Ala Gly Ala Gly Ser Gly Ala Gly Ala Gly Ser Gly
785                 790                 795                 800

Ala Gly Ala Met Asp Pro Gly Arg Tyr Gln Asp Leu Arg Ser His His
            805                 810                 815

His His His His
        820

<210> SEQ ID NO 5
<211> LENGTH: 810
<212> TYPE: PRT
<213> ORGANISM: Artificial Sequence
<220> FEATURE:
<223> OTHER INFORMATION: Combined copolymers of b. mori silk blocks and
      h. sapien elastin blocks with matrix metalloprotease
      (MMP)-responsive cleavage site

<400> SEQUENCE: 5

Gly Ala Gly Ser Gly Ala Gly Ala Gly Ser Gly Ala Gly Ala Gly Ser
1               5                   10                  15

Gly Val Gly Val Pro Gly Val Gly Val Pro Gly Val Gly Val Pro Gly
            20                  25                  30

Val Gly Gly Pro Gln Gly Ile Phe Gly Gln Pro Gly Lys Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
            85                  90                  95

Val Pro Gly Val Gly Val Pro Gly Ala Gly Ala Gly Ser Gly Ala Gly
            100                 105                 110
```

-continued

```
Ala Gly Ser Gly Ala Gly Ala Gly Ser Gly Ala Gly Ser Gly
            115                 120                 125
Ala Gly Ala Gly Ser Gly Ala Gly Ser Gly Ala Gly Ala Gly
            130                 135                 140
Ser Gly Ala Gly Ala Gly Ser Gly Val Gly Val Pro Gly Val Gly Val
145                 150                 155                 160
Pro Gly Val Gly Val Pro Gly Val Gly Pro Gln Gly Ile Phe Gly
            165                 170                 175
Gln Pro Gly Lys Gly Val Pro Gly Val Pro Gly Val Gly Val
            180                 185                 190
Pro Gly Val Gly Val Pro Gly Val Gly Val Pro Gly Val Gly Val Pro
            195                 200                 205
Gly Val Gly Val Pro Gly Val Gly Val Pro Gly Val Gly Val Pro Gly
            210                 215                 220
Val Gly Val Pro Gly Val Gly Val Pro Gly Val Gly Val Pro Gly Ala
225                 230                 235                 240
Gly Ala Gly Ser Gly Ala Gly Ala Gly Ser Gly Ala Gly Ala Gly Ser
            245                 250                 255
Gly Ala Gly Ala Gly Ser Gly Ala Gly Ala Gly Ser Gly Ala Gly Ala
            260                 265                 270
Gly Ser Gly Ala Gly Ala Gly Ser Gly Ala Gly Ala Gly Ser Gly Val
            275                 280                 285
Gly Val Pro Gly Val Gly Val Pro Gly Val Gly Val Pro Gly Val Gly
            290                 295                 300
Gly Pro Gln Gly Ile Phe Gly Gln Pro Gly Lys Gly Val Pro Gly Val
305                 310                 315                 320
Gly Val Pro Gly Val Gly Val Pro Gly Val Gly Val Pro Gly Val Gly
            325                 330                 335
Val Pro Gly Val Gly Val Pro Gly Val Gly Val Pro Gly Val Gly Val
            340                 345                 350
Pro Gly Val Gly Val Pro Gly Val Gly Val Pro Gly Val Gly Val Pro
            355                 360                 365
Gly Val Gly Val Pro Gly Ala Gly Ala Gly Ser Gly Ala Gly Ala Gly
            370                 375                 380
Ser Gly Ala Gly Ala Gly Ser Gly Ala Gly Ala Gly Ser Gly Ala Gly
385                 390                 395                 400
Ala Gly Ser Gly Ala Gly Ala Gly Ser Gly Ala Gly Ala Gly Ser Gly
            405                 410                 415
Ala Gly Ala Gly Ser Gly Val Gly Val Pro Gly Val Gly Val Pro Gly
            420                 425                 430
Val Gly Val Pro Gly Val Gly Gly Pro Gln Gly Ile Phe Gly Gln Pro
            435                 440                 445
Gly Lys Gly Val Pro Gly Val Gly Val Pro Gly Val Gly Val Pro Gly
            450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Val Gly
            485                 490                 495
Val Pro Gly Val Gly Val Pro Gly Val Gly Val Pro Gly Ala Gly Ala
            500                 505                 510
Gly Ser Gly Ala Gly Ala Gly Ser Gly Ala Gly Ala Gly Ser Gly Ala
            515                 520                 525
Gly Ala Gly Ser Gly Ala Gly Ala Gly Ser Gly Ala Gly Ala Gly Ser
```

-continued

```
                530                 535                 540
Gly Ala Gly Ala Gly Ser Gly Ala Gly Ala Gly Ser Gly Val Gly Val
545                 550                 555                 560

Pro Gly Val Gly Val Pro Gly Val Gly Val Pro Gly Val Gly Gly Pro
                565                 570                 575

Gln Gly Ile Phe Gly Gln Pro Gly Lys Gly Val Pro Gly Val Gly Val
                580                 585                 590

Pro Gly Val Gly Val Pro Gly Val Gly Val Pro Gly Val Gly Val Pro
                595                 600                 605

Gly Val Gly Val Pro Gly Val Gly Val Pro Gly Val Gly Val Pro Gly
                610                 615                 620

Val Gly Val Pro Gly Val Gly Val Pro Gly Val Gly Val Pro Gly Val
625                 630                 635                 640

Gly Val Pro Gly Ala Gly Ala Gly Ser Gly Ala Gly Ala Gly Ser Gly
                645                 650                 655

Ala Gly Ala Gly Ser Gly Ala Gly Ala Gly Ser Gly Ala Gly Ala Gly
                660                 665                 670

Ser Gly Ala Gly Ala Gly Ser Gly Ala Gly Ala Gly Ser Gly Ala Gly
                675                 680                 685

Ala Gly Ser Gly Val Gly Val Pro Gly Val Gly Val Pro Gly Val Gly
                690                 695                 700

Val Pro Gly Val Gly Gly Pro Gln Gly Ile Phe Gly Gln Pro Gly Lys
705                 710                 715                 720

Gly Val Pro Gly Val Gly Val Pro Gly Val Gly Val Pro Gly Val Gly
                725                 730                 735

Val Pro Gly Val Gly Val Pro Gly Val Gly Val Pro Gly Val Gly Val
                740                 745                 750

Pro Gly Val Gly Val Pro Gly Val Gly Val Pro Gly Val Gly Val Pro
                755                 760                 765

Gly Val Gly Val Pro Gly Val Gly Val Pro Gly Ala Gly Ala Gly Ser
    770                 775                 780

Gly Ala Gly Ala Gly Ser Gly Ala Gly Ala Gly Ser Gly Ala Gly Ala
785                 790                 795                 800

Gly Ser Gly Ala Gly Ala Gly Ser Gly Ala
                805                 810
```

SILK-ELASTIN LIKE PROTEIN POLYMERS FOR EMBOLIZATION AND CHEMOEMBOLIZATION TO TREAT CANCER

RELATED APPLICATIONS

The present application is a divisional of U.S. patent application Ser. No. 14/150,652, which is titled "SILK-ELASTIN LIKE PROTEIN COPOLYMERS FOR EMBOLIZATION AND CHEMOEMBOLIZATION TO TREAT CANCER," filed Jan. 8, 2014, which claims priority to U.S. Provisional Appl. No. 61/848,673, titled INTRAVASCULAR IN-SITU GELLING PROTEIN POLYMER EMBOLIC AGENT, filed Jan. 8, 2013. Both of these applications are hereby incorporated by reference in their entireties.

STATEMENT REGARDING FEDERALLY SPONSORED RESEARCH

This invention was made with government support under Grant R41 CA168123 awarded by the National Institutes of Health. The government has certain rights in the invention.

TECHNICAL FIELD

The present disclosure relates generally to the field of treating cancer by blocking tumor vasculature with a protein hydrogel embolic agent that may also include a chemotherapeutic drug. The hydrogel may be configured to release chemotherapeutic drug into the tumor at a defined rate.

BRIEF DESCRIPTION OF THE DRAWINGS

FIG. 1A provides the amino acid sequence of two embodiments of SELPs as disclosed herein, SELP-47K and SELP-815K.

FIG. 2A illustrates the step of gaining vascular access in the subject.

FIG. 2B illustrates the step of selecting an artery that feeds the tumor for injecting the chemoembolic agent.

FIG. 2C illustrates the step of administering the chemoembolic to the tumor.

FIG. 6A depicts the in vitro microfluidic device with simulated blood flowing through the structures that simulate the vasculature.

FIG. 6B depicts the in vitro microfluidic device of FIG. 6A being injected with SELP-815K solution.

FIG. 6C depicts the in vitro microfluidic device of FIG. 6B being injected with simulated blood after injected SELP-815K has formed a hydrogel embolism.

BRIEF DESCRIPTION

Figure 1B:
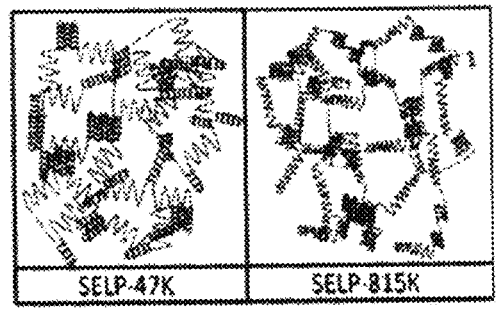
FIG. 1B illustrates the assumed network configuration of the SELPs of FIG. 1A.

The present disclosure relates generally to the field of embolics and drug delivery methods for treating cancer. More specifically, the present disclosure relates to the use of recombinantly synthesized silk-elastin-like protein (SELP) copolymers to embolize tumor vasculature, including the small vessels such as arterioles. The SELP solution is an injectable liquid at room temperature and forms a hydrogel in the tumor vasculature at body temperature. The material may be loaded with one or more chemotherapeutic drugs which may be released into the tumor from the embolic agent. The copolymers may also have matrix metalloprotease cleavage sites engineered into the protein copolymer using recombinant techniques to enable controlled breakdown of the embolic material. This modification provides control over the duration of embolization and controlled release of the chemotherapeutic agent. Therefore, the material may attack the tumor both by depriving it of blood supply and/or by delivering chemotherapeutic compounds.

DETAILED DESCRIPTION

Hepatocellular carcinoma (HCC) is a cancer of the liver which, due to its relative lack of symptoms, is detected at advanced stages in 84% of cases. The 1-year survival rate of symptomatic HCC patients is 22% and at 5 years it is 5%. For these patients, the only curative option is surgical liver resection and liver transplantation. The lack of donor livers and the rapid progression of the disease, however, eliminates this option for most patients.

Several palliative treatment options can slow the progression of HCC and increase the survival time of patients. Because HCC is generally unresponsive to systemic chemotherapy, localized treatments such as local chemotherapy, radiotherapy, or ablative therapy are typically employed. The most widely used is transcatheter arterial chemoembolization (TACE). Using endovascular catheters to selectively access the arteries in the liver under radiographic imaging, the objectives of TACE are: 1) to deliver an embolizing agent to the arteries of the tumor(s), selectively blocking blood flow and causing ischemic necrosis, and 2) to co-deliver a chemotherapeutic agent or cocktail of agents, which concentrate in the tumor.

While TACE is the recommended first-line treatment option to increase survival times of patients with unresectable HCC, its effectiveness is dependent on a number of factors. Foremost among these factors is the physical and chemical nature of the embolizing agent. Liquid embolizing agents are the most easily injected through the smallest diameter catheters, consequently accessing the smaller, more tumor-selective arteries. Their drawback, at times, is that they may not be stably maintained in the arteries as liquids after injection as in the case of Lipiodol®, an iodized esterified oil, or as insoluble masses, as in the case of Onyx®, a liquid suspension of polyethylenevinylalcohol dissolved in DMSO. Embolizing agents consisting of particulate solids form more stable emboli, but are often more difficult to inject. They may require larger diameter catheters due to their large size (typically 200-1000 μm diameter particles), which limits the selectivity of the embolization.

TACE has been used to treat HCC with some success. However, there are several limitations to the current state of this technique. Collateral damage to healthy liver can arise from excessive non-tumor selective embolization or chemotherapeutic toxicity. For this reason, TACE is contraindicated for treatment of patients with multiple tumors (>2 tumors) or large tumors (>3 cm diameter). Such damage could be avoided and TACE treatment offered to more patients if embolization could be more selectively performed and chemotherapeutic delivery better controlled. Moreover, advances in the understanding of the physiology and pharmacology of hepatocellular carcinoma have led to the development of new potential drug therapies targeting the vascularization of HCC tumors. Attractive among these are the anti-angiogenic drugs targeting vascular endothelial growth factor, VEGF, and its receptor. However, these include high molecular weight therapeutics which cannot be effectively delivered using existing embolizing agents. An example is the biologic, bevacizumab, an anti-VEGF monoclonal antibody, which has a molecular weight of approximately 149 kD. An embolizing agent that is compatible with these drugs and capable of providing sustained delivery of high-molecular weight agents is needed.

Another factor affecting the efficacy of TACE is the duration of embolization. Ischemic necrosis as a result of embolization is important in controlling tumor growth. Using embolic agents composed of the synthetic polymers polyvinyl alcohol (PVA) or ethylene vinyl acetate (EVA) provides a permanent embolization. These polymers are non-degradable and can remain in tissues indefinitely. If an effective occlusion occurs immediately upon embolization and the occlusion is physically maintained (lack of recanalization), then blood flow to the target tissue will be permanently blocked. However, clinical outcomes are seldom clear-cut. After TACE, tumors have been found to respond to treatment for periods of up to several weeks to months, and then resume growth. Regardless of the reason, the opportunity to retreat a patient that experiences tumor rebound is the hallmark of sustained cancer treatment. Especially for unresectable HCC, which inherently responds poorly to systemic chemotherapy and for which retreatment options are limited, the blockage of blood flow from a previous TACE procedure further restricts these options in that intravascular access to the rebounding tumor is blocked. Restored blood flow to a previously embolized tumor in a treatment-relevant fashion would be clinically beneficial in treating unresectable HCC.

To be effective, an embolizing agent must be able to be selectively delivered to tumor arteries where it forms stable arterial occlusions. Ideal embolizing agents would likely take the form of a liquid with a viscosity low enough for injection through the smallest endovascular catheters (in some instances ≤500 μm inner diameter), enabling its flow into the smallest arteries, but high enough to restrict its flow through the capillaries and into systemic circulation. After injection, such liquid embolizing agents would transition to a solid hydrogel with enough physical strength to prevent its wash-out into the venous blood flow.

Such liquid embolizing agents and their hydrogels would also, ideally, be completely aqueous and compatible with the delivery of anti-cancer drugs, including high-molecular weight biotherapeutics, which are unable to be effectively delivered with current drug-eluting embolizing agents. Localized delivery to the tumor is important because therapeutics that effectively treat HCC and other tumors also often have undesired effects on other tissues. For example, new anti-angiogenic agents suppress tumor revascularization and regrowth, but may also suppress wound healing responses in patients with underlying wound pathologies such as extremity wounds in diabetic patients. Potent anti-proliferative drugs that target cells experiencing hypoxia could have significant effects on embolized liver tumors, however, they may also exacerbate the deterioration of heart and vascular tissues in patients with cardiovascular disease. Avoiding the off-target effects of these and other drugs by concentrating and localizing their release by delivering TACE according to the present disclosure could significantly advance new therapeutic options for HCC.

Novel arterial embolizing agents are disclosed herein which may elute drugs such as chemotherapeutic agents and which may possess one, two, or more of the properties of an ideal embolizing agent described above. The embolizing agents are injectable as a liquid, able to penetrate into the smallest arteries, and transform to an insoluble gel in-situ forming a substantially durable occlusion. The embolizing liquids are completely aqueous and compatible with drugs and biotherapeutics thus enabling their localized controlled release. The compositions are even compatible with live cells. The embolic agents are composed of the protein polymer, silk-elastin-like protein (SELP), a class of genetically engineered protein polymers which have been investigated for use in several different applications. SELPs are made up of repeating "blocks" of amino acids, referred to as "silk blocks" (Gly-Ala-Gly-Ala-Gly-Ser) (SEQ ID NO: 1) and "elastin blocks" (Gly-Val-Gly-Val-Pro) (SEQ ID NO: 2). The silk blocks consist of the sequence Gly-Ala-Gly-Ala-Gly-Ser (SEQ ID NO: 1), and are based on the naturally occurring fibrillar silk of B. mori, the common silkworm.

The design of the elastin blocks is based on mammalian elastin, a very common connective tissue in the body which gives skin its elasticity. With appropriate sequence and composition, SELPs transform from a liquid at room temperature (approximately 18-23° C.) to a physically cross-linked hydrogel network at body temperature (approximately 37° C.). SELPs have been described previously, including in PCT publication no. WO 2013/181471, which is incorporated herein by reference in its entirety. The viscosity and gelation rate of the SELP fluids are adjusted by specifying the composition and the concentration of the SELPs. The physical properties of the hydrogels, their polymer network densities and its stiffness, can be controlled by the SELP compositions (the silk to elastin ratio and the length of the silk and elastin block domains) and their solution concentrations.

FIG. 1A illustrates the amino acid sequences of SELP-47K and SELP-815K, two embodiments of SELPs that may comprise the chemoembolics as disclosed herein. The silk units forming the rigid backbone are in grey font and the flexible elastin units are shown underlined and in grey font. The elastin units allow pore formation which is required for drug release. FIG. 1B illustrates the assumed network configurations of SELP-47K and SELP-815K. As shown in FIG. 1B, the pore size of SELP-815K is larger than that of SELP-47K. Because pores size impacts the rate of drug release from the polymer, the size of the one or more chemotherapeutic molecule intended to be included in the chemoembolic agents may impact the optimal pore size for the hydrogels and, consequently, the optimal SELP compositions for drug delivery.

In addition to SELP structure, pore size of the network is affected by the concentration of the polymer. Therefore, both SELP structure and concentration can be optimized for drug release by adjusting either the choice of SELP polymer, its concentration, or both. In addition, the pore size, and thus the drug release rate, may be adjusted by blending different SELPs in combination. For example, a mixture of SELP-47K and SELP-815K may release a combination of low and high molecular weight drugs more effectively than either polymer alone.

Figures 2A, 2B, 2C:
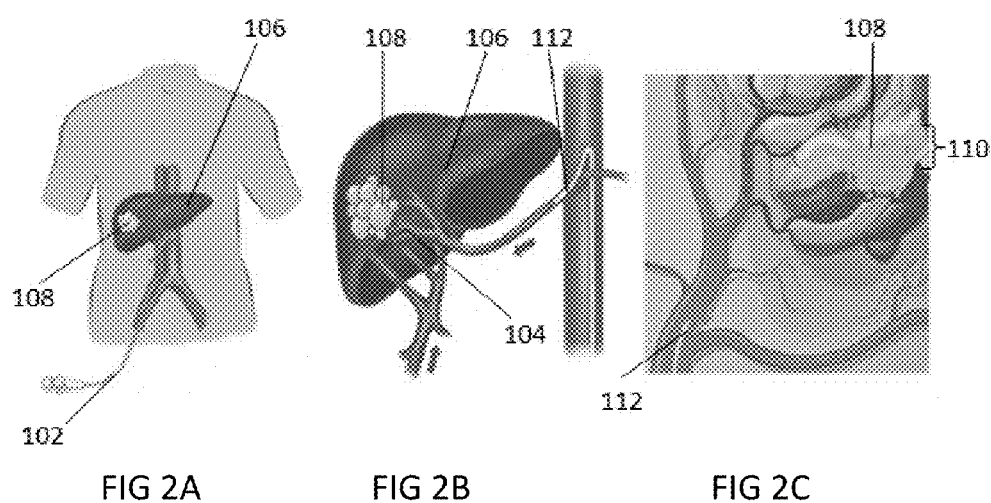
FIGS. 2A, 2B, and 2C, together, present a schematic depicting TACE treatment in a subject.

In addition, the present disclosure describes novel therapeutic methods comprising the steps of using endovascular catheters to selectively access the arteries in the tumor tissue under radiographic imaging, delivering the embolizing agents and/or chemoembolizing agents to the arteries of the tumor(s) by injecting the agent into the tumor vasculature, thus, selectively blocking blood flow causing ischemic necrosis, and, optionally, co-delivering a chemotherapeutic agent or cocktail of agents, which concentrate in the tumor(s). FIGS. 2A, 2B, and 2C illustrate a schematic of an embodiment of the methods of the present disclosure. FIG. 2A illustrates the step of gaining vascular access using an endovascular catheter 102. FIG. 2B illustrates the step of identifying and selecting the artery 104 in the liver 106 that feeds the tumor 108. The chemoembolic agent 110 will be injected into this artery 104. FIG. 2C illustrates the step of administering the chemoembolic agent 110 that comprises a drug or cocktail of drugs by injecting the chemoembolic agent 110 into the tumor vasculature through the selected artery 104. The tip 112 of the endovascular catheter 102 is shown within the selected artery 104 that feeds the tumor 108.

The present disclosure provides methods of treating cancer comprising the step of injecting a chemoembolic agent into the vasculature of a subject in need thereof using techniques including, but not limited to, that illustrated in FIGS. 2A, 2B, and 2C. The methods include a method of treating a cancer, wherein the cancer is hepatocellular carcinoma. Furthermore, the method may include the step of injecting a chemoembolic agent, wherein the at least one chemotherapeutic agent is effective against hepatocellular carcinoma.

In an alternative embodiment of the method illustrated in FIGS. 2A, 2B, and 2C, the SELP embolic agent is administered without chemotherapeutic agents or cocktails thereof. Because the SELPs in the disclosed agents are biodegradable, the agents may be administered repeatedly. Each time the embolic agent is administered, it may either include one or more chemotherapeutic agents or exclude such agents. In some embodiments, the steps of the disclosed method may alternate between administration of an embolic agent with one or more chemotherapeutic agents and administration of an embolic agent without a chemotherapeutic agent. Additionally, the one or more chemotherapeutic agents that comprise the chemoembolic agent may vary with each administration.

Embolization with SELPs may offer important advantages over the use of existing embolic agents. Unlike products composed of synthetic polymers, SELPs are proteins composed solely of natural amino acids and they will ultimately degrade to their constituent amino acids, which are non-toxic and biocompatible. Unlike the currently-available liquid embolics, such as Lipiodol® and Onyx®, the SELP formulations disclosed herein transition from liquids upon injection at room temperature (approximately 18-23° C.) to elastic hydrogels at body temperature (approximately 37° C.), forming stable biomaterials. The transition is not associated with any thermal release, nor is there a change of volume. Furthermore, the transition does not involve any chemical reaction, thus there is no possibility of chemically altering the chemotherapeutic agent(s). Unlike currently-available preformed particles, SELPs may be injected through finer catheters, enabling access to distal tumor-specific arteries. This increased precision of transcatheter delivery using a SELP liquid embolic may translate into more selective embolizations, potentially reducing collateral damage to the healthy tissue. Consequently, the novel TACE treatment disclosed herein may be applicable to a greater number of patients, including those with a greater number of tumors and/or greater tumor size than those currently treated with TACE. Furthermore, the SELP hydrogels eventually biodegrade, enabling subsequent TACE treatments, if necessary.

This disclosure also provides a method to further improve the drug delivery capability of SELPs by adding one or more matrix metalloprotease (MMP)-responsive peptide sequences to the monomer unit. Drug delivery rate is proportional to the rate the SELP polymer degrades. Adding MMP-responsive sequences may increase the rate of SELP polymer degradation and, thus, increase the drug delivery rate when the chemoembolic agent reaches the tumor.

MMPs are a family of structurally-related endopeptidases, which exist in a dynamic balance with tissue inhibitors of metalloproteases (TIMPs) to control myriad biological functions requiring extracellular matrix degradation. Proper function and regulation of MMPs is responsible for diverse biological functions such as angiogenesis, embryonic development, and wound healing. There are over 20 known specific MMPs, divided into subgroups based on their additional domains and known biological functions. The main classes of MMPs are collagenases, gelatinases, stromelysins, matrilysins, membrane-type MMPs, and other unclassified MMPs.

MMPs-2 and -9 are known as gelatinase type A and B, respectively, due to their known ability to degrade gelatin (denatured collagen). In normal situations, MMPs-2 and -9 contribute to many processes involving cell migration and signaling, including, for example, angiogenesis and inflammation/innate immunity. However, these MMPs have also been shown to be overexpressed in certain disease states relative to their expression in healthy tissue. The expression and activity of MMPs are increased in almost every type of human cancer, and this correlates with advanced tumor stage, increased invasion and metastasis, and shortened survival. HCC cells have been shown to produce MMPs including, but not limited to, MMPs-2 and -9.

The one or more MMP-specific cleavage sites may be chosen to correspond to the enzyme expressed by the relevant tumor. The sequence of each MMP-specific cleavage site will depend on the relevant MMP, regardless of the protein polymer used, and may be inserted in advantageous locations within the protein polymers.

In one embodiment of the disclosure, the chemoembolic agent is a SELP-815K copolymer including MMP cleavage sites. The one or more MMP cleavage sites in the SELP-815K protein polymer may comprise a cleavage site of either MMP-2, MMP-9, or of both MMP-2 and MMP-9. In some embodiments of the chemoembolic agent, the SELP copolymer comprises the following structure with the MMP-responsive sequence indicated by bold font:

[GAGS(GAGAGS)$_2$(GVGVP)$_3$GVGGPQGIFGQPGKGVP (SEQ ID NO: 5)

(GVGVP)$_{11}$(GAGAGS)$_5$GA]$_6$.

Figure 3:
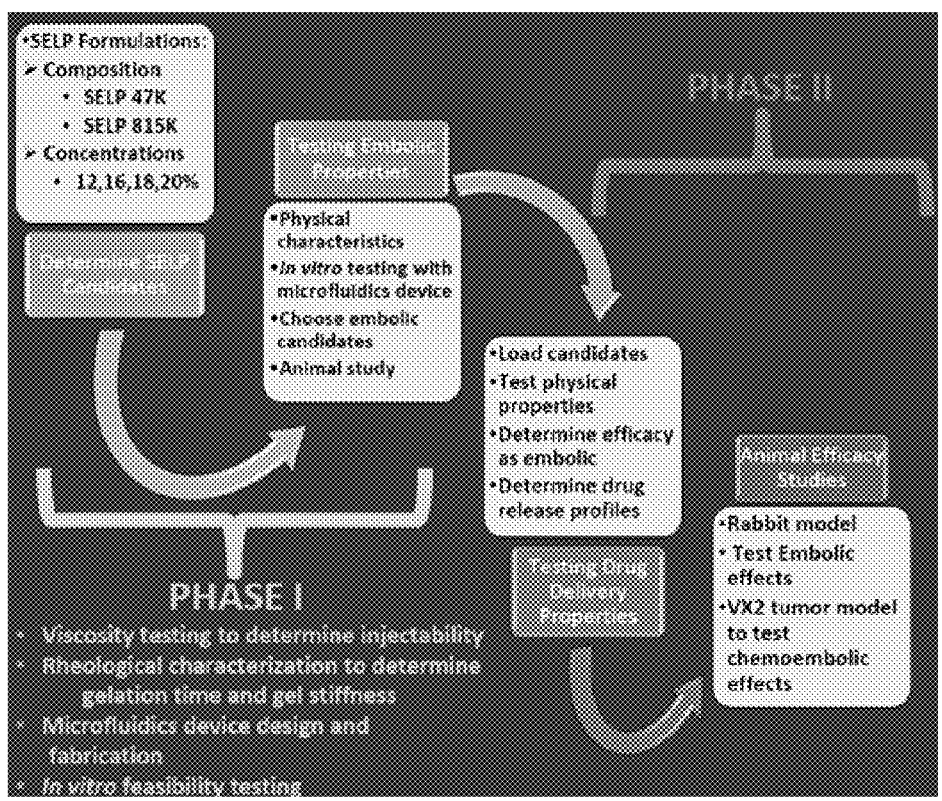
FIG. 3 depicts a flowchart that defines steps of a proposed method to identify and test a candidate formulation for a chemoembolic as disclosed herein.

Various embodiments of the disclosed protein polymer are within the scope of this disclosure. FIG. 3 presents a flowchart that shows the steps that may be taken to determine a candidate formulation of the chemoembolic agent as disclosed herein. The flowchart also includes steps that may be used to move the chemoembolic through feasibility testing of occlusive abilities. FIG. 3 also discloses steps that may be used to determine the drug delivery capabilities of the chemoembolic agent.

The method depicted in FIG. 3 comprises two phases. Phase I is designed to demonstrate the feasibility of a particular SELP formulation as an effective embolizing agent. Phase I begins with steps to be taken to identify SELP copolymer candidates that include (1) testing viscosity of varying concentrations of the SELPs to determine whether they may be injectable through a catheter, (2) rheological characterization to assess gelation time and gel stiffness so as to assess their ability to remain liquid at room temperature and transform to a transarterial embolism at body temperature, and (3) directly testing the feasibility in an in vitro system that mimics the vasculature. SELP solutions that are identified as candidates after being tested in Phase I proceed to Phase II, which is designed to test the ability of SELP formulations to deliver drugs to tumors. During Phase II, the manufacturing process of the selected SELP will be scaled up, the formulation optimized, product sterilization and packaging optimized, and drug release profiles evaluated. Implant safety and performance studies in suitable animal models may also be conducted.

The disclosure also describes a kit that may provide the components of the embolic and/or chemoembolic disclosed herein. The kit may comprise a SELP copolymer that is formulated to be used as an embolic as disclosed herein. One or more chemotherapeutic compounds may also be included in the kit. The SELP copolymer may be provided in liquid form or provided as a freeze dried or lyophilized powder along with a vial or ampoule of sterile water for reconstitution. The chemotherapeutic agent may also be provided in liquid form or provided as a freeze dried or lyophilized powder along with a vial or ampoule of sterile water for reconstitution. The SELP formulation and the one or more chemotherapeutic agents may be provided in the same or separate containers. A microcatheter for use in injection may be provided as may instructions for use of the kit.

EXAMPLES

The SELP-47K and SELP-815K copolymers used in the following examples were synthesized according to methods known in the art. While the examples disclosed herein characterize the use of SELP-47K and SELP-815K for use as chemoembolics, one of skill in the art will understand that these are but two embodiments of the protein polymers according to the present disclosure that may be formulated for use as embolics and/or chemoembolics.

Example 1. Viscosity of SELP-815K Formulations at Increasing Temperatures

Viscosity of the SELPs was determined using an AR 550 stress-controlled rheometer (TA Instruments, New Castle, Del.) with a cone-and-plate configuration using a 20 mm diameter, 4 degree cone. SELP copolymers were dissolved in phosphate buffered saline (PBS) at concentrations of 12%, 16%, 18%, or 20% w/w. The polymer solutions were mixed via vortex and manual inversion incrementally with cooling in ice every 30 s until dissolved (3-4 min.), followed by centrifugation at for 3 minutes at high speed in a clinical centrifuge (International Equipment Co.). Prepared polymer solutions were kept on ice until transfer to the Peltier plate of the rheometer. Generally, the elapsed time from which the PBS was added to the protein to the time in which the rheometer was started was about 30 to 45 minutes. A temperature ramp method was run starting at 1.5° C. and ending at 50° C., duration of 15 min and controlled angular velocity of 6.283 rad/s.

Figure 4A:
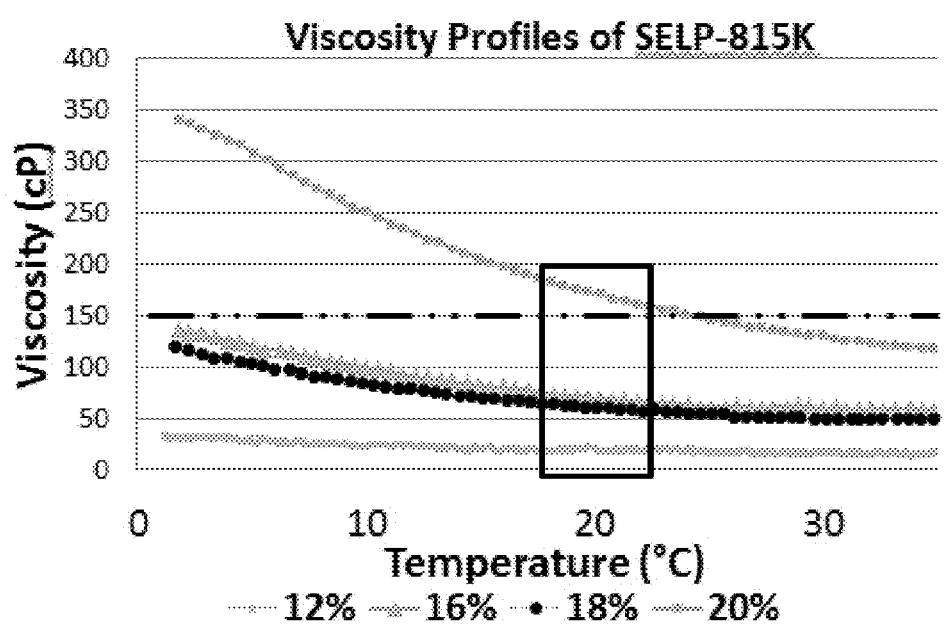
FIG. 4A is a graph that illustrates the viscosity profiles of different concentrations of SELP-815K.

FIG. 4A illustrates the effect of temperature and concentration on viscosity of SELP-815K. Viscosity levels that are compatible with injection were determined using silicone oil standards injected manually through 2.8° F. microcatheters using 1 cc and 3 cc syringes. Viscosity of all formulations increased as the temperature approached 37° C. The ideal viscosity is that which is injectable through a catheter of a desired size. A less viscous formulation may be injectable through a larger catheter. The viscosity of the formulation is optimally less than 1000 cP at room temperature (18-23° C.). A formulation of less than 500 cP may be used in situations where, for example, a somewhat smaller injection catheter is employed. However, it is desirable that the formulation maintain an even less viscous liquid form at room temperature (18-23° C.) in order to be able to pass through a microinjection catheter. Therefore, formulations that demonstrated a viscosity of equal to or less than 150 cP (indicated by the dashed and dotted line in FIG. 4A) at temperatures of 18-23° C. (identified as the box in FIG. 4A) were deemed most desirable as injectable embolic materials, at least in procedures employing microinjection catheters. One of skill in the art will readily optimize the viscosity of the liquid for the procedure at hand. As shown in FIG. 4A, solutions of 12, 16, and 18% w/w SELP-815K demonstrated a viscosity of equal to or less than 150 cP at temperatures of 18-23° C. while 20% w/w SELP-815K did not.

Figure 4B:
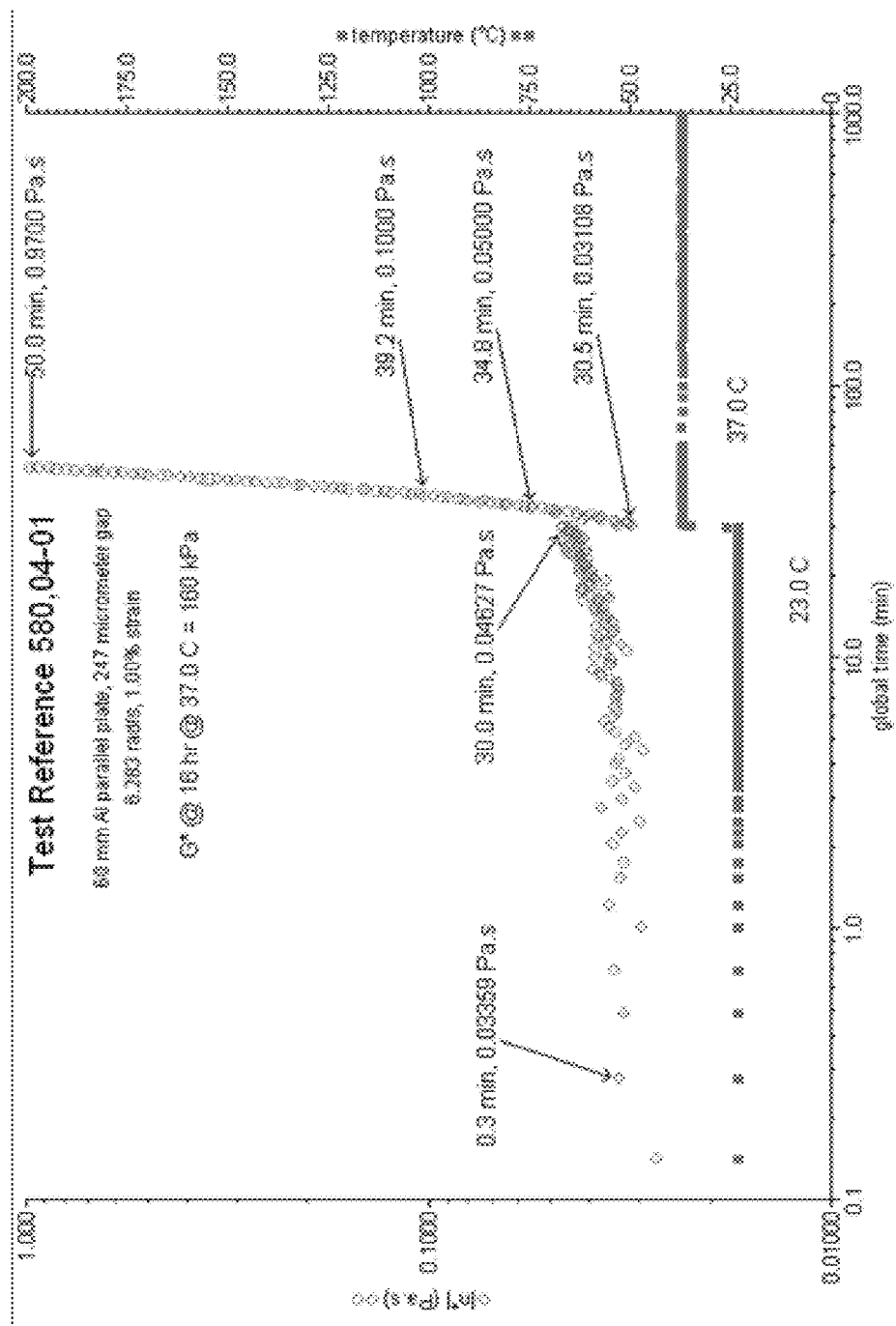
FIG. 4B illustrates the viscosity of 12% w/w SELP-47K during a thermal profile that simulated transcatheter injection.

Example 2. Assessment of Suitability of Viscosity of SELP-47K Formulation for Injection Through Intravascular Catheter A rheometer evaluation was conducted to determine if the viscosity of a SELP-47K solution could be obtained in the range suitable for catheter injection. The results of this experiment are shown in FIG. 4B. The viscosity of a 12% w/w SELP-47K solution for injection through a 1 m length× 0.5 mm internal diameter intravascular catheter using a 1 cc syringe with moderate hand pressure was determined empirically to be 50 cP. Rheometric analysis determined the viscosity of the SELP-47K fluid remained ≤46 cP at room temperature for up to 30 minutes (FIG. 4B, 1 cP=0.001 Pa·s). After 30 minutes, the temperature was shifted from room temperature to 37° C. The viscosity increased rapidly following the temperature shift but remained ≤50 cP for 4.8 minutes afterwards. The catheter had a hold-up volume of approximately 200 µl. At a minimum injection rate of 0.1 ml/min, the fluid residence time in the catheter would typically be 2 minutes. Therefore, the fluid in-transit through the catheter at 37° C. would remain fluid and injectable at a viscosity ≤50 cP throughout an anticipated 30-minute injection process.

Figure 4C:
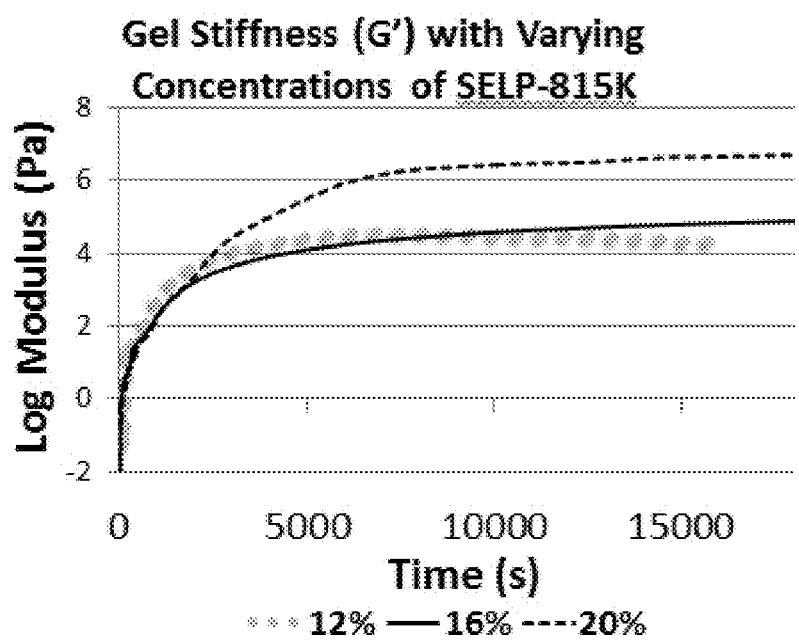
FIG. 4C is a graph that illustrates the gel stiffness of varying concentrations of SELP-815K over time as it forms a hydrogel.

Example 3. Assessment of Stiffness of Gels Formed by Formulations of SELP-815K FIG. 4C illustrates the results of an experiment that was conducted to assess gel stiffness (G') of varying concentrations of SELP-815K over time as it formed a hydrogel. A rheometer evaluation was conducted as in Example 1 to assess the strength of hydrogels formed from SELP-815K at concentrations of 12, 16, or 20% w/w. Oscillatory time sweeps were performed on each sample consisting of an equilibration time sweep at 23° C. and angular frequency of 6.283 rad/s and 1.0% strain for 1 minute followed by a 16 hour sweep at 37° C. and angular frequency of 6.283 rad/s and 0.1% strain. Briefly, individual polymer samples previously prepared to the correct concentration and kept on ice were immediately transferred to the Peltier plate pre-heated to 23° C. at a volume of 150 µl. The equilibration step ends with a temperature ramp up to 37° C. ranging 30-60 seconds before start of the 16 hour run. The time sweep result in traces for G' and G", the storage and loss moduli respectively. The G' plateau represents dynamic gel strength, formulations of 12 and 16% w/w SELP-815K showed similar stiffness within the time assessed in the experiment. In contrast, 20% w/w SELP-815K formed a more stiff gel. This experiment demonstrates that the stiffness of the hydrogels formed by the SELP solutions may be modified and optimized by varying the concentration of the solutions.

Figure 4D:
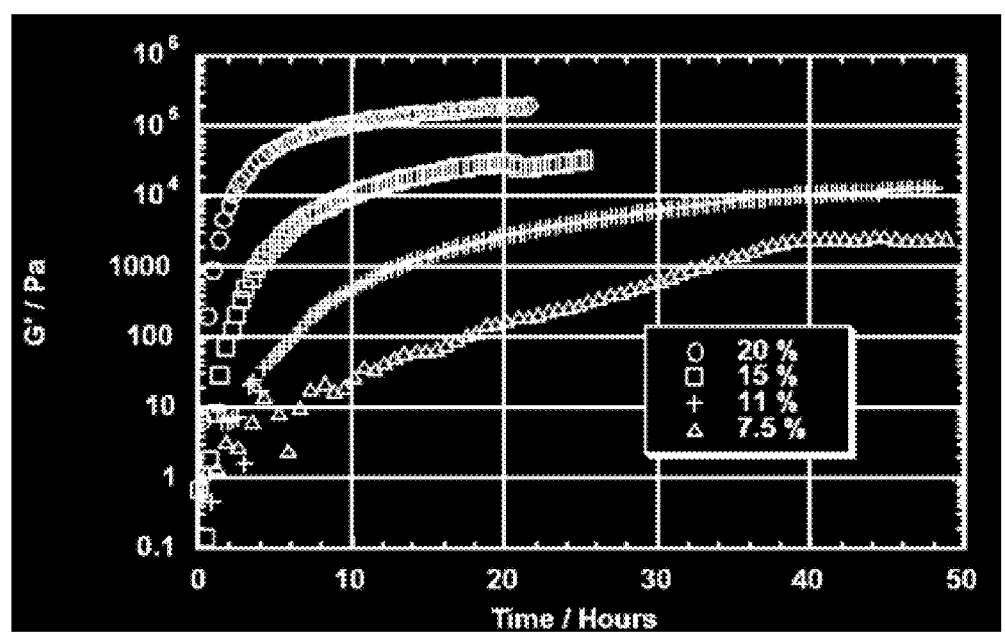
FIG. 4D is a graph that illustrates the gelation rates of varying concentrations of SELP-47K over time as they form hydrogels at 37° C.

Example 4. Assessment of Relationship Between SELP Concentration and Solution Viscosity The relationship between SELP concentration and solution viscosity as it relates to catheter injectability was determined by measuring the solution viscosity of SELP-47K at various concentrations ranging from 7.5 to 20% w/w. Viscosity was measured as described in Example 1. The storage modulus (G') for each sample was measured as a function of time at 37° C. This concentration range yielded SELP-47K solutions that are injectable through hypodermic needles and that undergo hydrogel formation (FIG. 4D).

Figure 5:
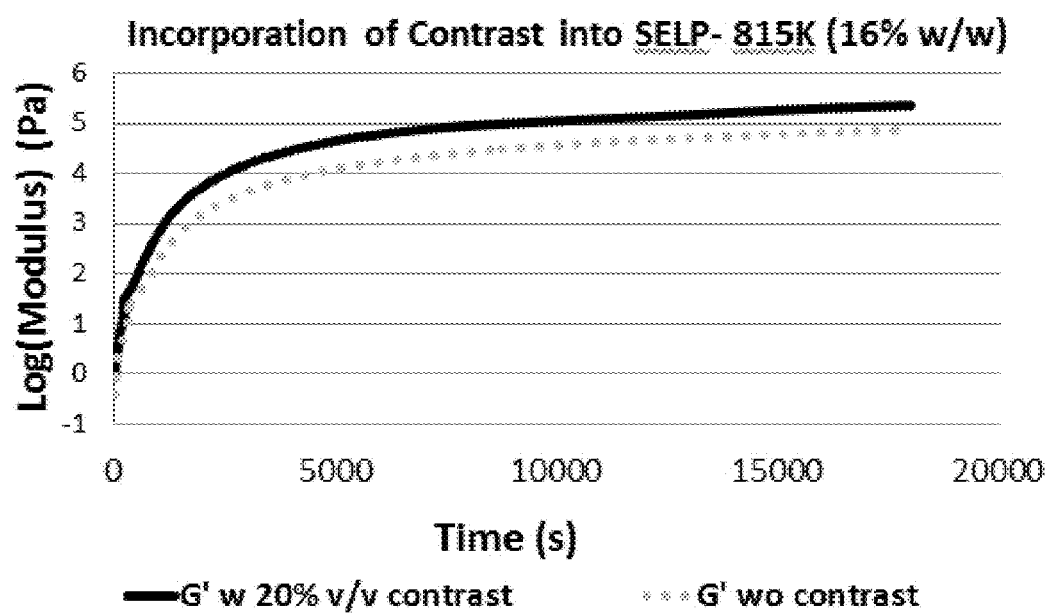
FIG. 5 is a graph that demonstrates the incorporation of contrast agent into 16% w/w SELP-815K for use in guiding a transarterial catheter during administration of the embolic agent.

Example 5. Assessment of Contrast Agent Incorporation into SELP-815K Solution During administration, the embolic and/or chemoembolic solutions will be injected into a tumor vasculature using a transarterial microcatheter. Contrast agent may be added to the solutions to guide the transarterial catheter during this process. Consequently, in some methods, SELP formulations that retain their gel strength when mixed with contrast agent are desirable. To assess the effect of contrast agent on gel strength, a solution of SELP-815K at a concentration of 16% w/w was prepared. Contrast agent was added to one sample of the solution at a concentration of 20% w/w contrast agent. The stiffness of the SELP-815K solution with and without contrast agent was assessed as in Example 3. FIG. 5 depicts a graph that demonstrates the incorporation of contrast agent into 16% w/w SELP 815K and its impact on gel stiffness. The gel formed from the SELP-815K solution that included contrast agent was similar in stiffness to that formed from SELP-815K solution without contrast agent. Consequently, the SELP-815K formulation tested is compatible with the addition of contrast agent for use in guiding the transarterial catheter during embolic and/or chemoembolic agent administration.

Example 6. In Vitro Evaluation of Embolic Capabilities of SELP-815K

Figure 6A:
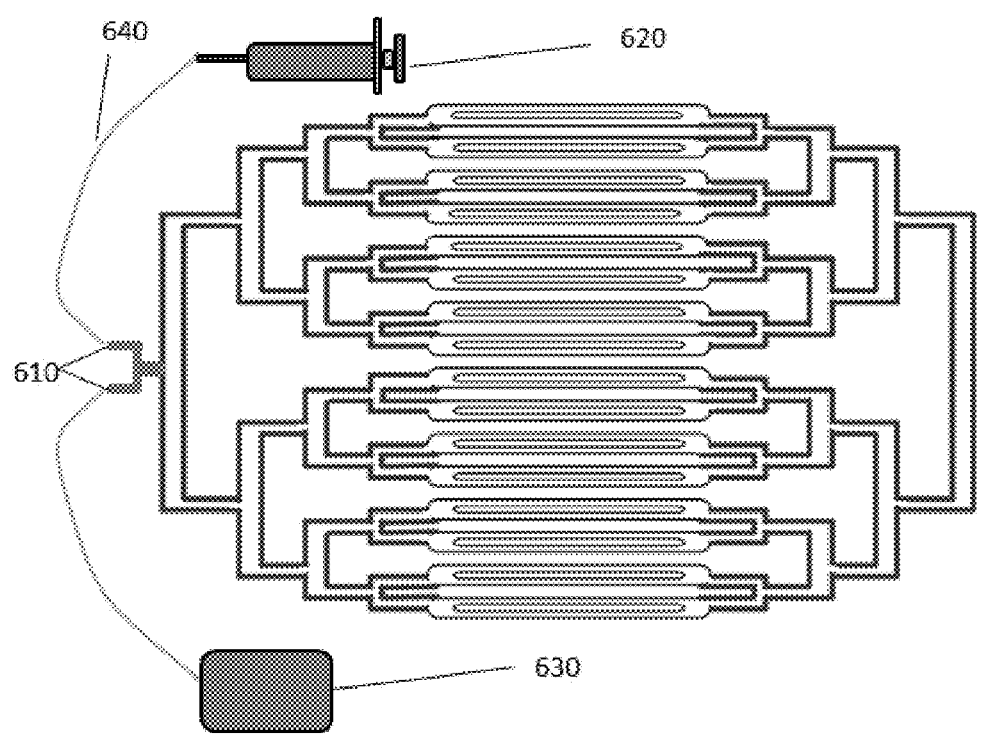
FIGS. 6A, 6B, and 6C illustrate the in vitro microfluidic system used to assess the ability of the embolic agent to occlude the microvasculature.

An in vitro test system was developed to evaluate the performance of a 16% w/w SELP-815K solution in embolization. This system comprised a custom microfluidic device to simulate arterio-capillary geometry and flow. It consists of a tapered occlusion channel with a proximal internal diameter of 1 mm at the entry and a distal internal diameter of 0.05 mm at the center. FIG. 6A illustrates the geometry of the microfluidic device. The device has two entry ports 610, a Luer Lok port for injection of the SELP test solution using a syringe 620 and microcatheter 640 and a second entry port for delivery of saline via a syringe pump 630 (see FIG. 6A). The delivery channels merge and enter the occlusion channel at the proximal end. A pressure gauge monitored the internal hydrostatic pressure.

Figure 6B:
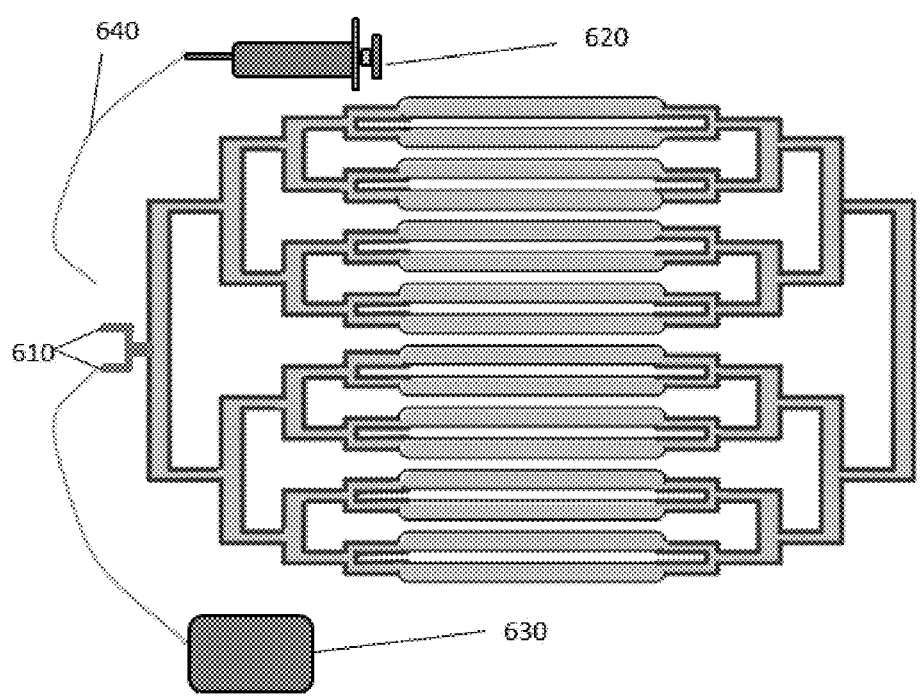
Figure 6C:
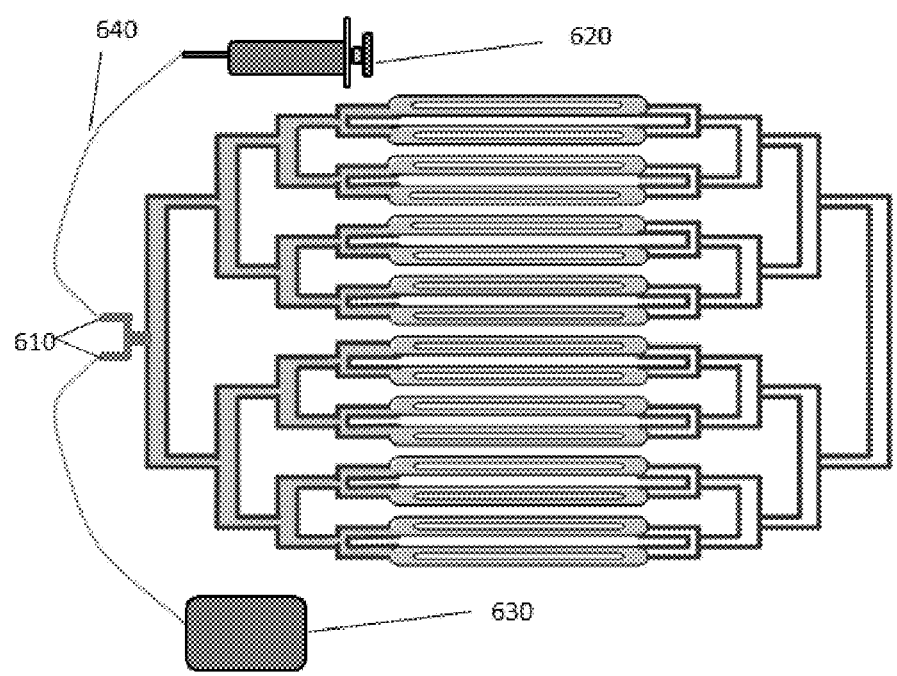

The experiment was conducted to verify that the SELP solutions have sufficient viscosity to prevent their flow through the occlusion channel. Three devices were connected in parallel as described above were set up to create a low pressure system mimicking hepatic vasculature. Colored saline designed to simulate blood was injected into one system at a rate of 3.4 ml/min. Internal hydrostatic pressure was maintained below 20 mm Hg. The fluid was able to permeate through the devices without blockage (see FIG. 6B, note that no SELP solution has entered the system as indicated by the detached microcatheter 640). The second device was injected with SELP-815K using syringe 620 and microcatheter 640 (see FIG. 6C) under flow conditions. The SELP-815K solution gelled, and blocked flow of the colored saline. The SELP hydrogel effectively blocked the solution from proceeding through the system (FIG. 6C). This result suggests that the SELP-815K solution (16% w/w) is sufficient to embolize small arteries such as those within tumor vasculature.

All publications cited in this specification are herein incorporated by reference as if each individual publication were specifically and individually indicated to be incorporated by reference herein and as though fully set forth.

Modifications and improvements of the embodiments specifically disclosed herein are within the scope of the following claims. Without further elaboration, it is believed that one skilled in the area can, using the preceding description, utilize the present disclosure to its fullest extent. Therefore the Examples herein are to be construed as merely illustrative and not a limitation of the scope of the present invention in any way. The embodiments disclosed in which an exclusive property or privilege is claimed are defined as follows.

We claim:

1. A method for blocking blood flow to a tumor present in a subject, the method comprising injecting into the tumor vasculature of the tumor an injectable aqueous embolic composition consisting of a silk-elastin like protein copolymer and an optional contrast agent, wherein the embolic composition does not include a chemotherapeutic agent, and wherein the silk-elastin like protein copolymer forms a hydrogel in the tumor vasculature and blocks blood flow to the tumor.

2. The method of claim 1, wherein the subject has heptacellular carcinoma.

3. The method of claim 1, wherein the embolic composition is administered to the subject by a catheter.

4. The method of claim 3, wherein the catheter is an endovascular catheter.

5. The method of claim 1, wherein the concentration of the silk-elastin like protein copolymer in the embolic composition is from 7.5% to 20% w/w, wherein the silk-elastin like protein copolymer is SELP-47K.

6. The method of claim 1, wherein the concentration of the silk-elastin like protein copolymer in the embolic composition is from 12% to 20% w/w, wherein the silk-elastin like protein copolymer is SELP-815K.

7. The method of claim 1, wherein the injectable aqueous embolic composition consists of phosphate buffered saline and the silk-elastin like protein copolymer is SELP-47K or SELP-815K.

8. The method of claim 1, wherein the silk-elastin like protein copolymer is SELP-815K.

* * * * *